United States Patent
Gerber et al.

(10) Patent No.: US 9,061,099 B2
(45) Date of Patent: Jun. 23, 2015

(54) CARDIOVASCULAR MONITORING FOR FLUID REMOVAL PROCESSES

(75) Inventors: Martin Gerber, Maple Grove, MN (US); John Burnes, Coon Rapids, MN (US); Suping Lyu, Maple Grove, MN (US); Manda R. VenKatesh, Stillwater, MN (US); Bryant Pudil, Plymouth, MN (US)

(73) Assignee: Medtronic, Inc., Minneapolis, MN (US)

(*) Notice: Subject to any disclaimer, the term of this patent is extended or adjusted under 35 U.S.C. 154(b) by 77 days.

(21) Appl. No.: 13/424,490

(22) Filed: Mar. 20, 2012

(65) Prior Publication Data
US 2012/0277650 A1 Nov. 1, 2012

Related U.S. Application Data (60) Provisional application No. 61/480,539, filed on Apr. 29, 2011, provisional application No. 61/480,544, filed on Apr. 29, 2011, provisional application No. 61/480,541, filed on Apr. 29, 2011, provisional
(Continued)

(51) Int. Cl.
*A61M 37/00* (2006.01)
*C02F 1/44* (2006.01)
(Continued)

(52) U.S. Cl.
CPC ........... *A61M 1/1603* (2014.02); *A61M 1/1605* (2014.02); *A61M 1/1607* (2014.02); *A61B 5/0031* (2013.01); *A61B 5/026* (2013.01);
(Continued)

(58) Field of Classification Search
CPC ............ A61M 1/1603; A61M 1/3607; A61M 1/3609; A61M 1/1601; A61M 1/1605; A61M 1/1607; A61B 5/4875; A61B 5/14539; A61B 5/4836

USPC ............... 604/5.01, 5.04, 6.09, 6.11, 4.01; 210/645, 646
See application file for complete search history.

(56) References Cited

U.S. PATENT DOCUMENTS 4,374,382 A 2/1983 Markowitz
4,556,063 A 12/1985 Thompson et al.
(Continued)

FOREIGN PATENT DOCUMENTS

WO 0066197 A1 11/2000
WO 01/70307 A1 9/2001
(Continued)

OTHER PUBLICATIONS

Sean M. Bagshaw, Rinaldo Bellomo, Prasad Devarajan, Curtis Johnson, C. J. Karvellas, D. James Kutsiogiannis, Ravindra Mehta, Neesh Pannu, Adam Romanovsky, Geoffrey Sheinfeld, Samantha Taylor, Michael Zappitelli, & R. T. Noel Gibney. Review article: Renal support in critical illness, Can J Anesth/J Can Anesth 57:999-1013 (2010).*

(Continued)

*Primary Examiner* — Leslie Deak
(74) *Attorney, Agent, or Firm* — Hahn & Voight PLLC; Roger C. Hahn; Kenneth J. Collier (57) ABSTRACT

A method includes initiating a blood fluid removal session for a patient in need thereof; monitoring a cardiovascular parameter of the patient; determining whether the indicator of the cardiovascular state crosses a predetermined threshold; and altering a parameter of the blood fluid removal session if the indicator is determined have crossed the threshold.

19 Claims, 9 Drawing Sheets

Related U.S. Application Data application No. 61/480,535, filed on Apr. 29, 2011, provisional application No. 61/480,532, filed on Apr. 29, 2011, provisional application No. 61/480,530, filed on Apr. 29, 2011, provisional application No. 61/480,528, filed on Apr. 29, 2011.

(51) Int. Cl.

| | | |
|---|---|---|
| *A61M 1/16* | (2006.01) | |
| *A61B 5/00* | (2006.01) | |
| *A61B 5/026* | (2006.01) | |
| *A61B 5/053* | (2006.01) | |
| *A61B 5/145* | (2006.01) | |
| *A61M 1/34* | (2006.01) | |
| *B01D 65/02* | (2006.01) | |
| *A61M 1/00* | (2006.01) | |
| *A61B 5/0295* | (2006.01) | |
| *A61M 1/14* | (2006.01) | |
| *B01D 61/00* | (2006.01) | |
| *B01D 61/32* | (2006.01) | |
| *A61M 1/36* | (2006.01) | |

(52) U.S. Cl.
CPC .............. *A61B 5/0537* (2013.01); *A61B 5/145* (2013.01); *A61B 5/4848* (2013.01); *A61B 5/6866* (2013.01); *A61B 2560/0223* (2013.01); *A61M 1/16* (2013.01); *A61M 1/342* (2013.01); *B01D 65/02* (2013.01); *A61M 2205/18* (2013.01); *A61M 2205/3334* (2013.01); *A61M 2205/70* (2013.01); *B01D 2321/12* (2013.01); *B01D 2321/40* (2013.01); *A61B 5/053* (2013.01); *A61M 1/00* (2013.01); *A61B 5/0295* (2013.01); *A61M 1/14* (2013.01); *A61M 1/34* (2013.01); *A61B 5/14503* (2013.01); *A61B 5/14539* (2013.01); *A61B 5/14546* (2013.01); *A61B 5/4836* (2013.01); *B01D 61/00* (2013.01); *B01D 61/32* (2013.01); *A61M 2205/33* (2013.01); *A61M 2205/3523* (2013.01); *A61M 2205/52* (2013.01); *A61M 2205/60* (2013.01); *A61M 2230/00* (2013.01); *A61M 2230/208* (2013.01); *A61M 1/1601* (2014.02); *A61M 1/1613* (2014.02); *A61M 1/3607* (2014.02); *A61M 1/3609* (2014.02); *A61B 5/14535* (2013.01); *A61B 5/4875* (2013.01); *A61B 5/7282* (2013.01); *A61M 2202/0498* (2013.01); *A61M 2205/04* (2013.01); *A61M 2205/3303* (2013.01); *A61M 2205/50* (2013.01); *A61M 2230/207* (2013.01); *A61M 2230/65* (2013.01)

(56) References Cited

U.S. PATENT DOCUMENTS

| | | |
|---|---|---|
| 4,562,751 A | 1/1986 | Nason et al. |
| 4,678,408 A | 7/1987 | Nason et al. |
| 4,685,903 A | 8/1987 | Cable et al. |
| 5,080,653 A | 1/1992 | Voss et al. |
| 5,092,886 A * | 3/1992 | Dobos-Hardy ............ 623/23.65 |
| 5,097,122 A | 3/1992 | Colman et al. |
| 5,127,404 A | 7/1992 | Wyborny et al. |
| 5,683,432 A | 11/1997 | Goedeke et al. |
| 5,725,775 A * | 3/1998 | Bene et al. .................... 210/646 |
| 6,058,331 A | 5/2000 | King |
| 6,248,093 B1 | 6/2001 | Moberg |
| 6,362,591 B1 | 3/2002 | Moberg |
| 6,554,798 B1 | 4/2003 | Mann et al. |
| 6,555,986 B2 | 4/2003 | Moberg |
| 6,589,229 B1 | 7/2003 | Connelly et al. |
| 6,676,608 B1 | 1/2004 | Keren |
| 7,674,231 B2 | 3/2010 | McCombie et al. |
| 7,754,852 B2 | 7/2010 | Burnett et al. |
| 8,313,642 B2 * | 11/2012 | Yu et al. .......................... 210/85 |
| 2002/0042561 A1* | 4/2002 | Schulman et al. ............ 600/345 |
| 2005/0065760 A1 | 3/2005 | Murtfeldt et al. |
| 2006/0264894 A1 | 11/2006 | Moberg et al. |
| 2007/0175827 A1* | 8/2007 | Wariar ........................ 210/645 |
| 2007/0215545 A1 | 9/2007 | Bissler |
| 2007/0255250 A1 | 11/2007 | Moberg et al. |
| 2012/0016228 A1 | 1/2012 | Kroh et al. |

FOREIGN PATENT DOCUMENTS

| | | |
|---|---|---|
| WO | 2004/030716 A2 | 4/2004 |
| WO | 2004/030717 A2 | 4/2004 |

OTHER PUBLICATIONS

Secemsky, et. al., High prevalence of cardiac autonomic dysfunction and T-wave alternans in dialysis patients, Heart Rhythm, Apr. 2011, 592-598 : vol. 8, No. 4.

Roberts, The regenerative dialysis (REDY) sorbent system, Nephrology, 1998, 275-278 : 4.

Redfield, et. al., Restoration of renal response to atrial natriuretic factor in experimental low-ouput heart failure, Am. J. Physiol., 1989, R917-923 : 257.

Wei, et. al., Fullerene-cryptand coated piezoelectric crystal urea sensor based on urease, Analytica Chimica Acta, 2001, 77-85 : 437.

Rogoza, et. al., Validation of A&D UA-767 device for the self-measurement of blood pressure, Blood Pressure Monitoring, 2000, 227-231, 5(4).

PCT/US2012/034332 International Search Report, Jul. 5, 2012.

* cited by examiner

CARDIOVASCULAR MONITORING FOR FLUID REMOVAL PROCESSES

RELATED APPLICATION

This application claims priority to U.S. Provisional Application No. 61/480,539, U.S. Provisional Application No. 61/480,544, U.S. Provisional Application No. 61/480,541, U.S. Provisional Application No. 61/480,535, U.S. Provisional Application No. 61/480,532, U.S. Provisional Application No. 61/480,530, and U.S. Provisional Application No. 61/480,528, wherein each priority application was filed Apr. 29, 2011, wherein each priority application is hereby incorporated by reference in its entirety to the extent that it does not conflict with the disclosure presented herein.

FIELD

The present disclosure relates generally to devices, systems and methods for monitoring cardiovascular conditions of patients for which blood fluid removal is indicated, such as patients suffering from kidney disease or heart failure.

BACKGROUND

Patients who undergo hemodialysis or other procedures that remove fluid and waste products from the blood often die of cardiac complications. Many possible factors may contribute to such death, including stress placed on the heart due to the increased fluid volume in these patients. Increased fluid volumes and innate inability to remove waste products from the blood, in some cases, can also contribute to electrolyte and pH imbalance that can affect cardiac contractility and efficiency. Further, rapid changes in fluid volume or pH or electrolyte concentration of the blood during hemodialysis or other fluid removal processes may place additional stress on the heart and may contribute to the high rate of morbidity for patients who undergo blood fluid removal procedures.

Patients who undergo blood fluid removal procedures, such as hemodialysis, typically have a number of cardiovascular parameters such as blood pressure, heart rate or heart rhythm parameters that are outside of general population norms. For example, Secemsky et al., have shown that a patient population undergoing chronic hemodialysis had a prevalence of abnormal heart rate variability of 82%, a prevalence of abnormal heart rate turbulence of 75%, and a prevalence of T-wave alternans of 96%, which are all indicators of heightened probability of sudden cardiac death (Heart Rhythm, vol. 8, no. 4, pp. 592-598, April 2011).

Typically, chronic hemodialysis patients undergo periodic examinations that allow a healthcare provider to set various parameters of the blood fluid removal procedures, such as the profile of fluid removal, the composition of dialysate or replacement fluid employed, and the like. With current standards of care, these examinations occur about once a month, absent any pressing health issues with the patient. However, hemodialysis or similar procedures may occur three to four times a week. Thus, the patient may undergo 10 to 15 or more blood fluid removal sessions before the prescription or parameters are changed. It is possible, for example, that a prescription with regard to dialysate or replacement fluid composition will not be appropriate for a patient several days or weeks after the prescription is set. Accordingly, it may be desirable to more frequently determine whether the blood fluid removal prescription is appropriate. In addition, it may be desirable to adjust parameters during a blood fluid removal session in a manner that may improve patient health and reduce morbidity.

SUMMARY

This disclosure, among other things, describes devices, systems and methods for monitoring cardiovascular conditions of patients for which blood fluid removal sessions are indicated, and using data acquired from the monitoring to alter the blood fluid removal sessions. The monitored data may be acquired between blood fluid removal sessions to adjust the prescription to account for the cardiovascular state of the patient closer in time to the blood fluid removal session, as opposed to days or weeks removed from the session. The monitored data may be acquired during a session and parameters of the blood fluid removal session may be adjusted during the session based on the acquired data. As the parameters of the session are being adjusted, cardiovascular monitoring may be continued to determine whether the patient is responding favorably to the adjustments of the fluid removal parameters. By monitoring cardiovascular parameters, more appropriate initial fluid removal parameters may be used, or the fluid removal parameters may be adjusted during a session, to enhance patient safety.

In various embodiments described herein, a method includes initiating a blood fluid removal session for a patient in need thereof; monitoring a cardiovascular parameter (such as heart rate, hearth rhythm, or blood pressure) of the patient; determining whether the indicator of the cardiovascular state crosses a predetermined threshold; and altering a parameter of the blood fluid removal session if the indicator is determined have crossed the threshold. In embodiments, the predetermined threshold is based on measurements of the cardiovascular parameter obtained prior to initiating the blood fluid removal session.

The method may also include monitoring the cardiovascular parameter of the patient prior to initiating the blood fluid removal session, and setting an initial prescription for the blood fluid removal session based on the cardiovascular parameter monitored prior to initiating the blood fluid removal session. The initial prescription for the blood fluid removal session may include a fluid removal prescription or a dialysate or replacement fluid composition prescription.

In embodiments described herein, a system includes a blood fluid removal device, a sensor for monitoring a cardiovascular parameter of a patient, and control electronics that may, in some embodiments, be housed within the blood fluid removal device. The blood fluid removal device includes an inlet for receiving blood from a patient; an outlet for returning blood from the patient; a medium for removing fluid and contaminants from the blood, wherein the medium is positioned between the inlet and the first outlet; and a control element for controlling the rate at which fluid is removed from the blood by the medium. The control electronics are in operable communication with the sensor and the control element and are configured, via the control element, to adjust the rate at which the fluid is removed from the blood.

In embodiments described herein, a system includes a blood fluid removal device, a sensor for monitoring a cardiovascular parameter of a patient, a concentrate source for housing a concentrate solution comprising a concentrated component for the fluid, a concentrate flow control element for controlling the rate that the concentrate solution enters the fluid source, and control electronics that may, in some embodiments, be housed within the blood fluid removal device. The blood fluid removal device includes (i) an inlet for receiving blood from a patient; (ii) an outlet for returning blood from the patient; (iii) a medium for removing fluid and contaminants from the blood, wherein the medium is positioned between the inlet and the first outlet; and (iv) a fluid source for carrying a fluid, such as dialysate or replacement fluid. If the fluid is dialysate, the fluid source carries the fluid to the medium. If the fluid is replacement fluid, the fluid source carries the fluid to the blood after the blood exits the medium. The control electronics are in operable communication with the sensor and the concentrate flow control element and are configured, via the concentrate flow control element, to adjust the rate at which the concentrate solution enters the fluid source based on data obtained from the sensor.

One or more embodiments of the systems, devices and methods described herein may provide one or more advantages over prior systems, devices and methods for blood fluid removal in patients. Such advantages will be apparent to those of skill in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

FIGS. 8-9 are schematic block diagrams showing flow paths and some control mechanisms (closed loop: FIG. 8; open loop: FIG. 9) for controlling flow of concentrate into fluid for use in a blood fluid removal process based on monitored pH or electrolytes.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

As used herein, a "patient for which a blood fluid removal session is indicated" is a patient that has undergone, is undergoing, or is likely to undergo at least one blood fluid removal session. In general, such patients are fluid overloaded patients, such as patients suffering from heart failure, chronic kidney disease, or acute renal failure. Often such patients are stage 3 to stage 5 chronic kidney disease patients, are unresponsive or under-responsive to diuretics, or the like.

As used herein, a "blood fluid removal process," or the like, refers to a process from which fluid, or fluid and solutes, is removed from blood of a patient and the blood is returned to the patient. In most cases, the blood is also cleaned; i.e., waste products are removed from the blood, and the cleaned blood is returned to the patient. Examples of such processes include ultrafiltration, hemofiltration, hemodialysis, peritoneal dialysis, hemodiafiltration, and the like. Any patient for which blood fluid removal is indicated may benefit from the devices, systems and methods described herein.

This disclosure relates to, among other things, devices, systems and methods for monitoring cardiovascular conditions in patients for which blood fluid removal sessions are indicated, and using data acquired from the monitoring to alter the blood fluid removal sessions. Sensors are used to monitor the cardiovascular conditions of the patient. The sensors may be implanted in the patient, wearable or external to the patient. In embodiments, an initial prescription for a blood fluid removal procedure is set based on data acquired from the sensors. In embodiments, parameters of the blood fluid removal process are altered during a session based on data acquired from the sensors during the session. As the parameters of the session are being adjusted, cardiovascular monitoring may be continued to determine whether the patient is responding favorably to the adjustments of the fluid removal parameters.

Any suitable device or system for removing fluid, or fluid and contaminants, from blood may be used in accordance with the teachings presented herein. The devices, or components thereof, may be traditional large counsel-type, wearable, or implantable.

Figure 1:
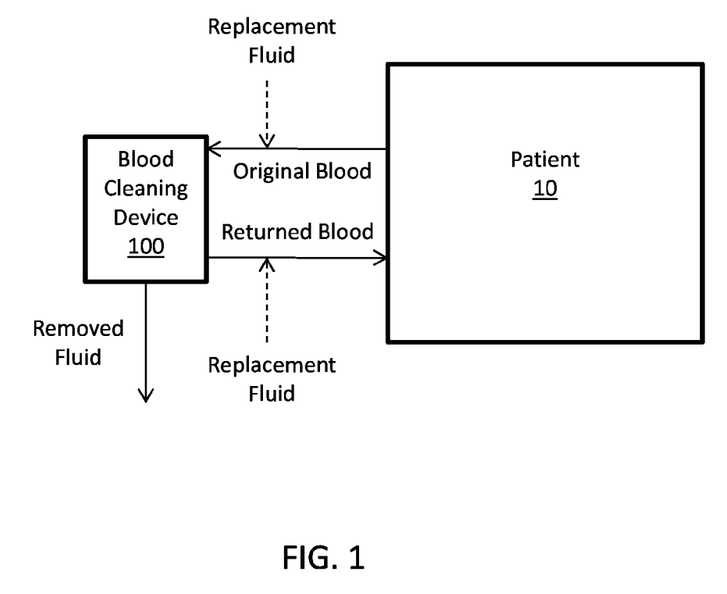
FIGS. 1-3 are schematic block diagrams showing interaction of blood fluid removal devices with a patient showing flow of blood (dashed arrows) and fluid (solid arrows), which blood fluid removal devices may be used in various embodiments described herein.
Figure 2:
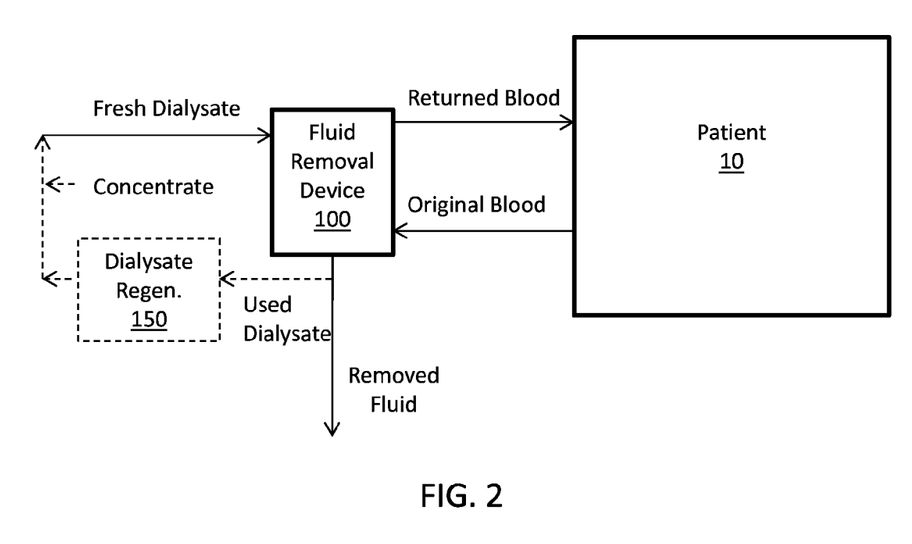
Figure 3:
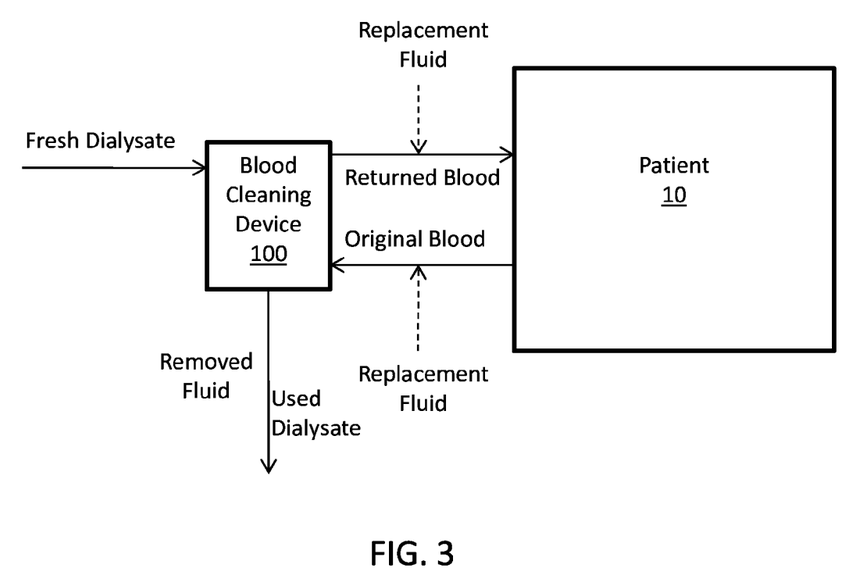

Block diagrams of some examples devices and systems are shown in FIGS. 1-3. As shown in FIG. 1, blood may be removed from a patient 10 and fluid may be removed via a blood fluid removal device 100 and returned to the patient 10. Removed fluid may be diverted. In some embodiments where the blood fluid removal device 100 or system, or components thereof, are implanted, the removed fluid may be diverted to the patient's bladder. Examples of blood fluid removal devices 100 that may operate as depicted in FIG. 1 are ultrafiltration and hemofiltration devices. Examples of such devices and components thereof that may be employed in accordance with the teachings presented herein are well known in the art. It will be understood that peritoneal dialysis, where dialysate is introduced into the peritoneal cavity, may also be employed.

With some of such devices, replacement fluid may be introduced into the patient's blood as fluid is removed from the blood by the device 100 at too great of a rate or amount. The replacement fluid may be added to the original blood before fluid removal or may be added to the blood after initial fluid removal and prior to return to the patient's cardiovascular system. Preferably, the replacement fluid is added after initial fluid removal. The pH and electrolyte concentration of the replacement fluid may be set or adjusted, e.g. as described in more detail below, based on monitoring of cardiac conditions of the patient.

As shown in the embodiment depicted in FIG. 2, the blood fluid removal device 100 may employ dialysate to assist in removal of contaminants from the patient's blood and in maintaining proper pH and electrolyte balance. The pH or electrolyte concentration of the dialysate may be set or adjusted, e.g. as described in more detail below, based on monitoring of pH or electrolytes. Used dialysate and fluid removed from the blood may be diverted. In some embodiments, particularly where the blood fluid removal device 100 or system or components thereof are wearable or implantable, the used dialysate and removed fluid, or a portion thereof, may be regenerated (indicated by dashed lined regeneration system 150) to produce fresh dialysate for re-use in the blood fluid removal process. One system for regeneration of dialysate is the REDY system, such as described in Roberts, M, "The regenerative dialysis (REDY) sorbent system," *Nephrology* 4:275-278, 1998, which system may be employed or readily modified for use in embodiments described herein. As shown in FIG. 2, a concentrate may be added to the regenerated dialysate to adjust the pH and electrolytes of the regenerated dialysate to an amount suitable for re-use as fresh dialysate.

Regardless of whether the dialysate is regenerated, systems and devices that operate in a manner shown in the embodiment of FIG. 2 include hemodialysis and hemodiafiltration systems. Examples of such devices and components thereof that may be employed in accordance with the teachings presented herein are well known in the art. It will be understood that peritoneal dialysis, where the dialysate is introduced into peritoneal cavity may also be employed.

As shown in FIG. 3, in cases where the blood fluid removal device 100 of FIG. 2 removes fluid from the blood at too high of a rate, replacement fluid may be introduced into the patient's blood, upstream or downstream of fluid removal, e.g. as described above with regard to FIG. 1.

Regardless of the device or blood fluid removal process employed, it may be important have an appropriate initial fluid removal prescription and electrolyte concentration of the dialysate or replacement fluid that reflects the cardiovascular state of the patient on the day of, or close to the day of, the fluid removal session. It may also be desirable to control the parameters of the fluid removal session based on the status of the patient's cardiovascular system during the session. By monitoring a cardiovascular condition of a patient and setting or altering parameters of a blood fluid removal session based on the monitored condition, it may be possible to decrease adverse cardiac events in patients who undergo blood fluid removal sessions.

The ranges of concentrations of electrolytes or pH buffers in dialysate or replacement fluid may vary to achieve a target pH and electrolyte concentration in the blood following a blood fluid removal session. Typical ranges of pH and blood electrolyte concentration that are desired during or following a blood fluid removal session are provided in Table 1 below.

TABLE 1

Ranges for pH and electrolytes
(ref. Medical Surgical Nursing, 7th Ed., 2007)

|  | Target Range |
|---|---|
| pH | 7.35-7.45 |
| Phosphate | 2.8-4.5 mg/dL |
| Bicarbonate | 22-26 mEq/L |
| $Cl^-$ | 96-106 mEq/L |
| $mg^{2+}$ | 1.5-2.5 mEq/L |
| $Na^+$ | 135-145 mEq/L |
| $K^+$ | 3.5-5.0 mEq/L |
| $Ca^{2+}$ | 4.5-5.5 mEq/L |

However, it will be understood that the target for a particular patient may be different from the values presented in Table 1 for one or more electrolyte or pH. It will also be understood that buffers are typically employed to maintain proper blood pH.

Some suitable buffers that may be used in fluid, such as replacement fluid or dialysate, include bicarbonate, citrate, acetate, lactate, amino acid and protein buffers. The concentration and composition of the buffers and components thereof may be adjusted based on monitored cardiac conditions. Similarly, the concentration of electrolytes such as sodium, potassium, calcium, and chloride in replacement fluid or dialysate may be set or altered based on the monitored cardiac conditions.

The methods, systems and devices described herein may be used, in some embodiments, to set the initial electrolyte concentration and pH (buffer components and concentration) based on monitoring that occurs before a blood fluid removal session starts. In some embodiments, the monitoring is chronic; e.g., monitoring is performed intermittently, periodically or continuously over the course of days, weeks, months or years. In an attempt to minimize interference with the patient's lifestyle, the monitoring system, or components thereof, may be implantable or wearable.

Figure 4:
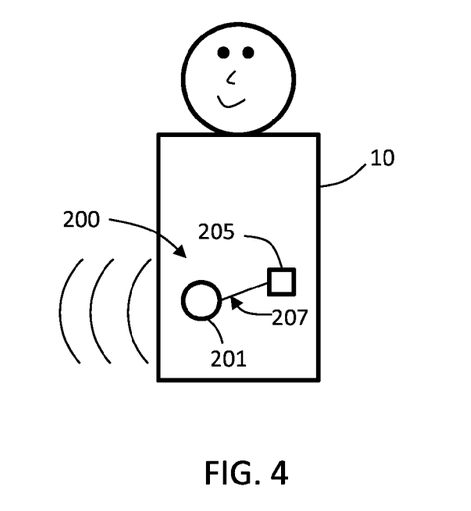
FIG. 4 is a schematic diagram of an embodiment of a sensor device implanted in a patient.
Figure 5:
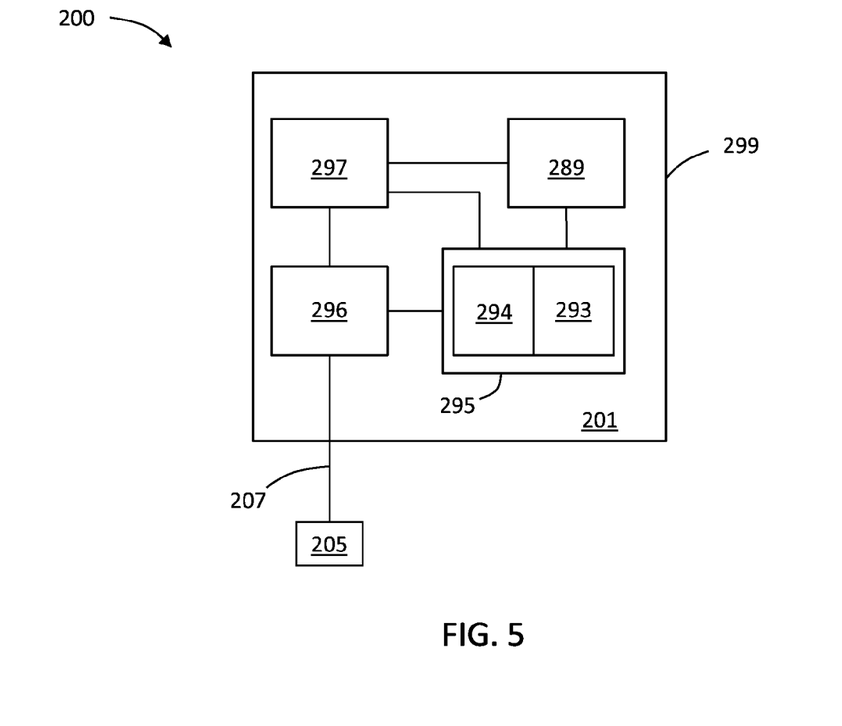
FIG. 5 is a schematic block diagram showing some selected components of an embodiment of a sensor device.
Figure 6:
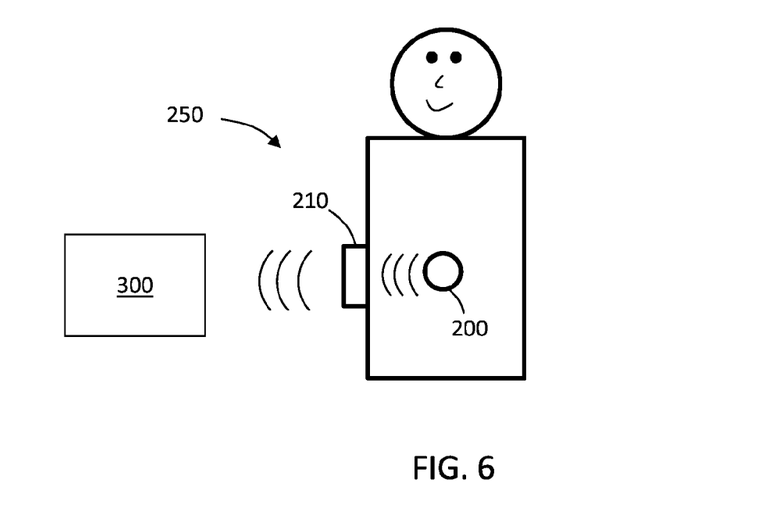
FIG. 6. is a schematic diagram of an embodiment of a implanted sensor device configured to communicate with an external device, which is configured to communicate with a remote device.

For example and with reference to FIGS. 4-6, embodiments of monitoring devices or systems that have implantable or wearable components are shown. In the embodiment depicted in FIG. 4, sensor device 200 is fully implantable in the patient 10 and is capable of communicating with devices outside of the patient or other implanted devices via telemetry or other suitable form of communication. The sensor 200 includes a device body 201 containing electronic components within a hermetically sealed housing. A sensing component 205, such as an electrode, is operably coupled to the electronics of the device body 201 via a lead 207. In this manner the device body 201 may be implanted at a location removed from the sensing component 205. In some embodiments, the sensor 200 is leadless and the transducer is incorporated into the device body 210 or a portion thereof, such as a portion of the housing. The sensing component 205, whether in a leadless or lead-containing device 200, is preferably placed in a location of the body where it is capable of sensing appropriate signals regarding the cardiac condition.

For example, if the sensor device 200 is configured to detect heart rate or heart rhythm parameters, the sensing component 207 may be placed in proximity to the heart of at any other location of the patient 10 where such signals may be detected. One suitable implantable sensor device that is configured to monitor a patient's ECG signals is a Medtronic, Inc.'s Reveal® series insertable cardiac monitor. In embodiments, the sensor device may be a suitably equipped pacemaker or defibrillator already implanted in the patient. Monitored cardiac signals from such a device may be transmitted to a blood fluid removal device or intermediate device for use in the blood fluid removal session or for setting the prescription for the blood fluid removal session.

If the sensor device 200 is configured to detect blood pressure, the sensing component 207 is preferably placed within or about a blood vessel. An example of a leadless pressure sensor device that is capable of being placed in blood vessel of a patient is Medtronic, Inc.'s active leadless pressure sensor (ALPS), which generally takes the form of a stent to anchor the device within vessel. Such a device may be placed in any suitable blood vessel location, such as in a femoral artery or pulmonary artery.

For purposes of illustration, a block diagram of an implantable sensing device 200 (e.g., as depicted in FIG. 4) is shown in FIG. 5. The depicted sensor is implantable and has a hermetically sealed housing 299 for containing various electronic components 296, 297, 289, 295. Sensing circuitry 296, such as analog-to-digital convertor, band-pass filter, or the like, is operably coupled to power supply 297 and control electronics 295, which include a processor 294 and a memory 293 for storing sensed data and processor instructions. Sensing circuitry 296 is also operably coupled to sensing component 205, such as an electrode or pressure transducer, via lead 207, which enters housing 299 via a hermetic feedthough (not shown). Control electronics 295 are also operably coupled to power supply 297, which may be a battery or the like, and to telemetry circuitry 289 for wirelessly communicating with a device external to the patent or with another device implanted in the patient. In some embodiments, the telemetry circuitry 289 allows the sensor device 200 to transmit data regarding a monitored conditions directly to a blood fluid removal device or system that is equipped with suitable telemetry circuitry. In embodiments, the sensor device or components thereof are a part of an implantable blood fluid removal system.

Referring now to FIG. 6, an embodiment of a sensor system 250, in which the implanted sensor device 200 (leadless is shown, but may include lead as depicted in FIG. 4), communicates with an external device 210. The external device 210 may be worn and may carry out some processing of data acquired by sensor 200 to reduce power consumption of implanted sensor 200. The external device 210 may also communicate to remote devices 300. Of course, in some embodiments, the implanted sensor 200 may communicate directly with remote device 300.

Remote devices 300 may be devices associated with blood fluid removal and data transmitted by external device 210 may be used to set or adjust fluid pH and electrolyte concentrations and fluid removal profiles before or during a blood fluid removal session. Remote device 300 may be a computer, personal data assistant or the like connected to the internet or a phone network, allowing sensed data or other information regarding sensed data to be transmitted to a healthcare provider. For example, the sensed data, or information regarding the sensed data, may be used to prepare an appropriate initial fluid (e.g., dialysate or replacement fluid) for use in the patient's next blood fluid removal session. If the monitored cardiac condition is out of a predetermined range, an appointment to see a healthcare provider or to schedule a blood fluid removal session may be performed automatically. In some embodiments, remote device 300 is a physician programmer device. Of course, remote device 300 may be any other suitable device.

Figure 7:
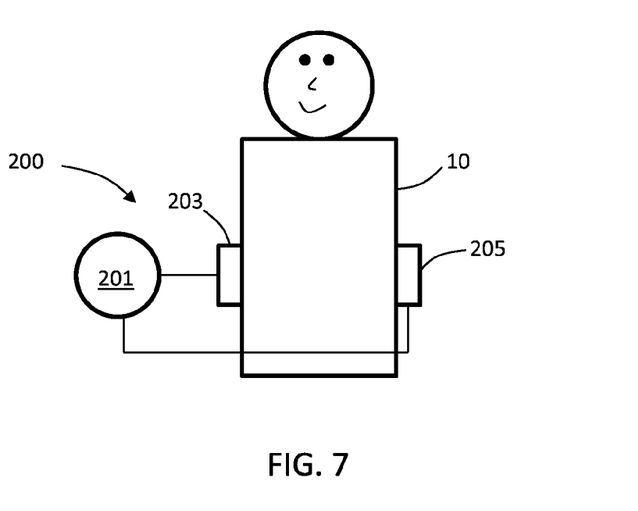
FIG. 7 is a schematic diagram of an embodiment of a sensor device that is wearable by a patient.

Referring now to FIG. 7, a wearable sensor system 200 is shown. The sensor system 200 includes a device body 201 containing appropriate electronic components (such as some electronic components discussed above with regard to FIG. 6) and one or more sensing components, 203, 205, such as electrodes or transducers. The sensing components 203, 205 are operably coupled to the electronic components in the device body 201, e.g. via leads as shown in FIG. 7. Any suitable sensor system may be employed, such as a Holter sensor system that is configured to monitor ECG activity of the patient 10. An example of a suitable wearable blood pressure monitoring system is a wearable blood pressure monitor described in U.S. Pat. No. 7,674,231, "Wearable Pulse Wave Velocity Blood Pressure Sensor and Methods of Calibration Thereof", issued Mar. 9, 2010.

As with the implanted sensing systems discussed above, a wearable sensing system may communicated with a blood fluid removal device, remote device, or implanted device, which may be an implanted blood fluid removal system, in any suitable manner. In embodiments, a wearable sensor system is a part of a wearable blood fluid removal system or device.

Regardless of whether the sensor 200 employed, or components thereof, is implantable, wearable, part of a larger stand-alone device, or part of a blood fluid monitoring device, the sensor may monitor any suitable cardiovascular parameter of a patient. In various embodiments, the sensors or monitoring systems are configured to monitor one or more of heart rate, heart rhythm or a variable thereof, or blood pressure. Examples of variables of heart rhythm that may be measured are heart rate variability (HRV), heart rate turbulence (HRT), T-wave alternans (TWA), P-wave dispersion, T-wave dispersion, Q-T interval, ventricular premature depolarization (VPD), or the like.

One or more of the monitored cardiovascular parameters may be employed to set an appropriate prescription for the patient's next blood fluid removal session or to adjust during a blood fluid removal session. As such cardiovascular parameters are well known, well studied and well documented; one of skill in the art will readily understand the ways in which a blood fluid removal session may be initiated or altered based on such parameters. By way of example, if the patient's blood pressure is high or higher than typical for the patient, the rate of fluid removal may be increased. If the blood pressure is low or lower than typical for the patient, the rate of fluid removal may be decreased. If the patient's heart rate is high (e.g., higher than a predetermined threshold), the dialysate potassium concentration may be increased.

However, it will be understood that potassium levels may be particularly important in the regulation of arrhythmias and that sudden changes in serum potassium concentration can precipitate arrhythmias. Accordingly, the initial concentration of potassium employed in dialysate or replacement fluid, in many embodiments, is similar to the starting potassium concentration in the patient, which can be determined by a sensor as described herein. Further, in some embodiments, changes in potassium concentration are made slowly in an attempt to avoid precipitation of an arrhythmic event. It will be further understood that changes in the fluid removal or electrolyte concentrations of dialysate or replacement fluid, other than changes in potassium, may be performed gradually, rather than abruptly, to attempt to avoid arrhythmic events, which may be precipitated by sudden changes.

Table 2 below provides some general examples of how an initial prescription or adjustments during a blood fluid removal session may be altered based on a monitored cardiovascular condition or parameter.

TABLE 2

Example alterations that may be taken based on cardiovascular monitoring

| Monitored Parameter | Status | Fluid Removal Rate | $K^+$ conc. | $Na^+$ conc. |
|---|---|---|---|---|
| Blood pressure | High | Increase | | Decrease |
| | Low | Decrease | | Increase |
| Heart rate | High | | Increase | |
| | Low | | Decrease | |
| Q-T interval | High | | Increase | |
| | Low | | Decrease | |

The status in Table 2 may refer to a monitored value relative to a predetermined threshold or relative to the particular patient's history. $Na^+$ concentration and $K^+$ concentration are concentrations of the fluid used in a blood fluid removal session, such as dialysate or replacement fluid. The concentrations may be adjusted from standard concentrations that may be typically employed (see, discussion above with regard to Table 1) that are particularly suited for the particular patient based on monitored data. In embodiments, the concentrations of electrolytes in dialysate or replacement fluid are initially closely matched to the concentrations of electrolytes in the patient at the start of the session and gradual changes are made toward target ranges; e.g., over the course of the session.

Monitoring of the one or more cardiovascular conditions may occur before, during or after a blood fluid removal session parameter is changed. If the patient's cardiovascular conditions continue to worsen following an adjustment, the blood fluid removal session change may be reversed or a different change may be made. If the patient's cardiovascular condition improves following the blood fluid removal session parameter change, the parameter change may remain in effect for a period of time or other changes may be made to determine whether further improvements are achievable. The blood fluid removal parameters may be changed one at a time, or more than one at a time may be changed, based on patient safety concerns or patient history. For example, if the patient has previously presented with a particular status of a particular condition or combination of conditions and has previously responded favorably to certain combinations of blood fluid session parameter adjustments, it may be desirable to simultaneously implement such adjustments. Systems and methods for basing parameters on patient history before, during or after a blood fluid removal session are described in Provisional Patent Application No. 61/480,539, entitled ADAPTIVE SYSTEM FOR BLOOD FLUID REMOVAL, and filed on the same day as the present application, which application is hereby incorporated herein by reference in its entirety.

Figure 8:
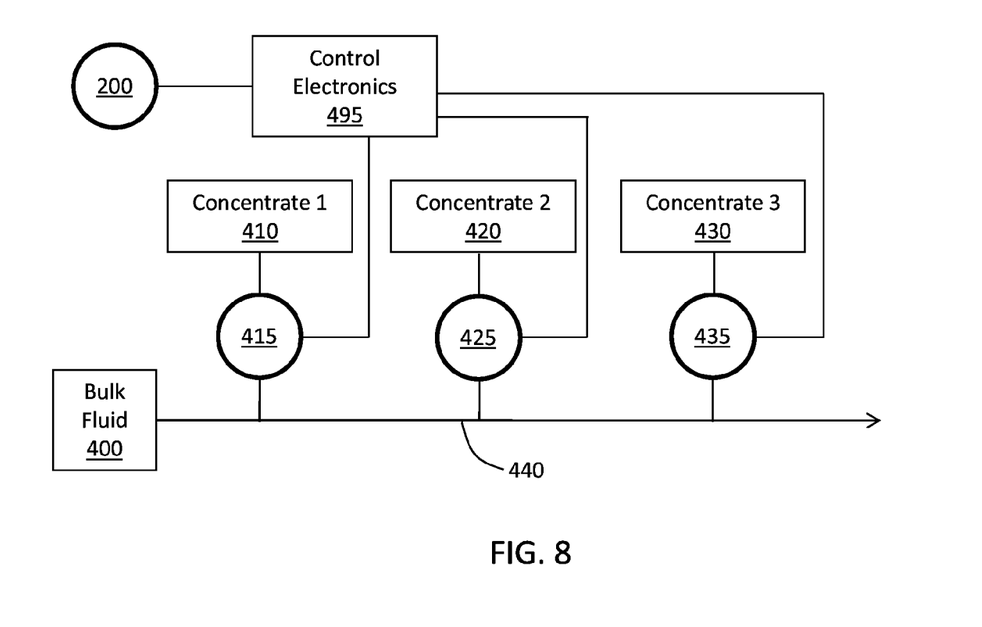
Figure 9:
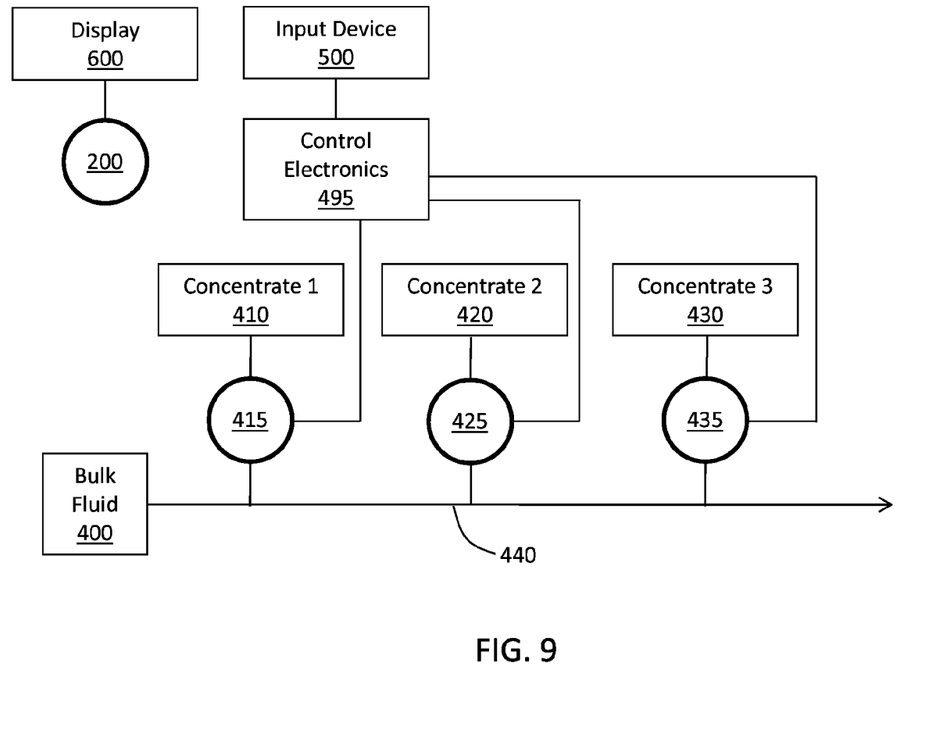

During a blood fluid removal session, the session parameters may be adjusted in any suitable manner to achieve the desired effect, such as changing rate of fluid removal or changing the composition of the fluid. By way of example, some representative components of a blood fluid removal system configured to control the composition (e.g., concentration of various components) of a fluid (dialysate or replacement fluid) for use in the blood fluid removal system are shown in FIGS. 8-9. FIG. 8 is an example of a closed-loop system, and FIG. 9 is an example of an open-loop system.

With reference to FIG. 8, data from sensor 200 is presented to control electronics 495, which are configured to control flow control elements 415, 425, 435, such as valves. The data from the sensor may be communicated to the control electronics 495 directly, e.g. via wired connection or telemetry, or indirectly via a device in communication with the sensor 200. The electronically controllable flow control elements 415, 425, 435 are in fluid communication with supplies of concentrated electrolyte or buffer solutions 410, 420, 430, or other concentrated components of dialysate or replacement fluid, and with fluid line 440, which may be a catheter for carrying fresh dialysate or a catheter for carrying replacement fluid. The electronically controllable flow control elements 415, 425, 435, via control electronics 495, control the rate at which the concentrates 410, 420, 430 flow into the fluid line 440. The concentrates 410, 420, 430 are added to bulk fluid 400 to adjust the concentration of components such as electrolytes of the bulk fluid (and thus the blood).

Referring now to FIG. 9, data from sensor 200 may be processed and appropriate information presented on a display 600, which may be a part of the blood fluid removal device, a separate computer, or the like. A healthcare provider may use the information presented on the display 600 to adjust the concentration of components, such as electrolytes. This can be done, for example, by transmitting appropriate instructions to the control electronics via an input device 500. Any suitable input device 500 may be used. For example, input device 500 may be a keyboard, a computer, a tablet, a personal data assistant, a physician programmer, or the like. In some embodiments, the input device 500 is the display 600; e.g., where the display 600 is a touch screen device. Regardless of how the instructions are input, the control electronics 495 can control flow control elements 415, 425, 435 to control the amount of concentrate 410, 420, 430 introduced to bulk fluid 400, which may be dialysate or replacement fluid.

Any number of suitable concentrates may be used. In embodiments, one concentrate is used. The one concentration may include, for example, one or more electrolytes that may be desirable to control. The use of more than one concentrate will allow independent control or more variables of the ultimate fluid composition, and may be desirable in certain circumstances.

Control elements 415, 425, 435 may be any suitable control element, such as electronically controllable valves, electronically controllable pump mechanisms, or the like.

Figure 10:
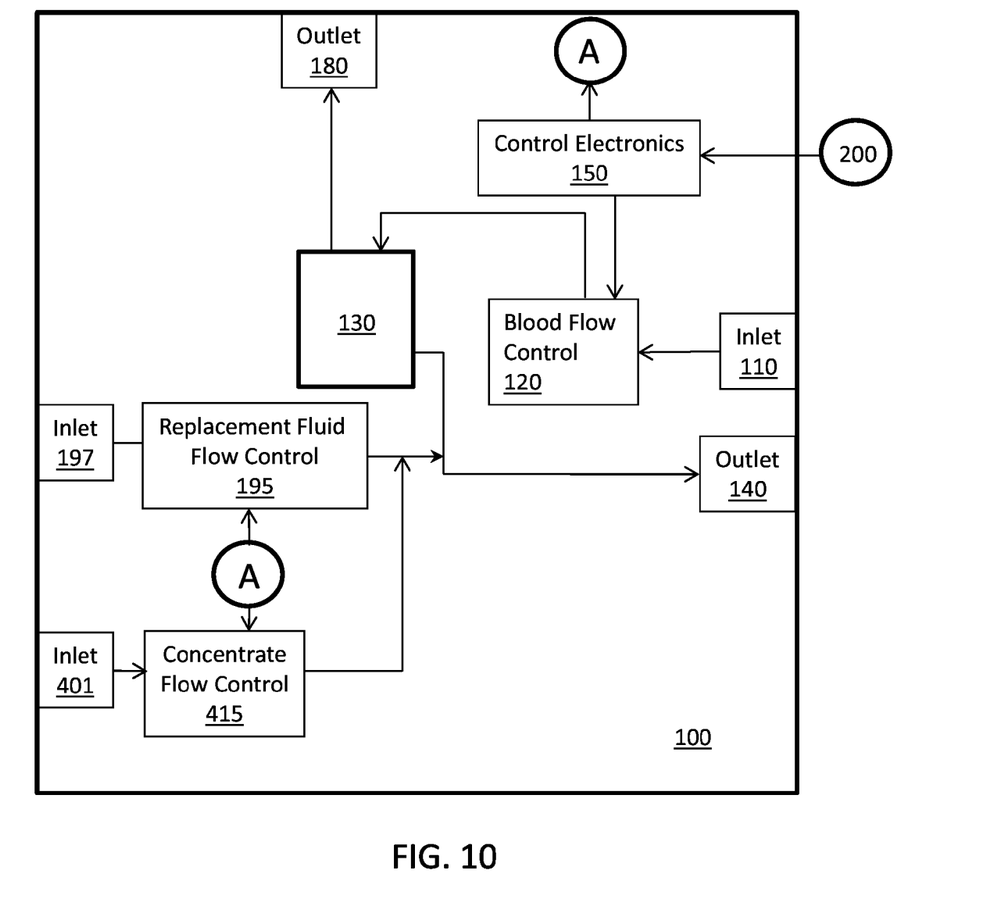
FIGS. 10-11 are schematic block diagrams of some components of blood fluid removal devices that are configured to adjust pH or electrolyte concentrations of fluids in response to data regarding monitored pH or electrolyte levels in blood.
Figure 11:
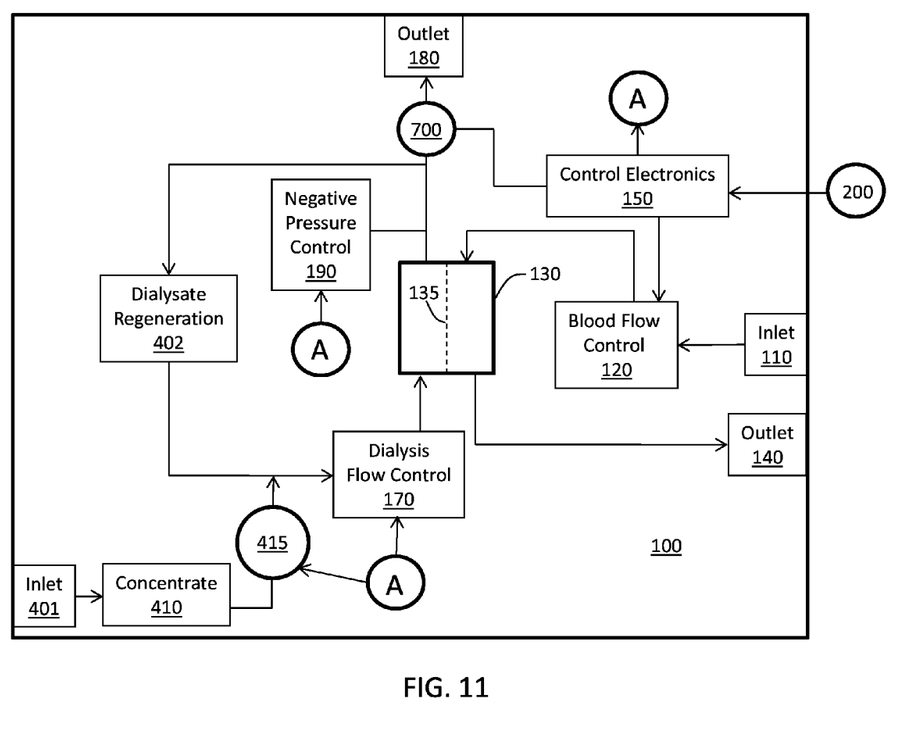

Any suitable system may be configured as depicted in FIGS. 8-9 to provide control of adjustment of component concentration based on data acquired from one or more sensors. By way of example, selected components of two example systems are illustrated in FIGS. 10-11. The system in FIG. 10 illustrates control of flow of a concentrate into replacement fluid, and the system in FIG. 11 illustrates control of flow of a concentrated into dialysate. FIGS. 10-11 also illustrate some example control mechanisms that may be employed to control the rate at which fluid may be removed from the blood of a patient.

Referring now to FIG. 10, the depicted device 100 includes a fluid pathway for adding replacement fluid to blood before it is returned to the patient. The device 100 includes an inlet 110 for receiving blood from the patient and an outlet 140 for returning blood to the patient. In the flow path between the inlet 110 and outlet 140 are a blood flow control element 120 and a medium for removing fluid and contaminants from the blood. The blood flow control element 120 is operably coupled to control electronics 150 which provide instructions to control the rate at which blood is passed through medium 130. Fluids and contaminants removed from the blood by the medium 130 may exit via outlet 180.

The device 100 depicted in FIG. 10 also includes an inlet 197 for receiving bulk replacement fluid and a replacement fluid flow control element 195 in communication with the inlet and configured to control the rate at which the replacement fluid is added to the blood. The control electronics 150 are operably coupled to the replacement fluid flow control element 195 and are configured to control the rate at which replacement fluid flow control element 195 adds fluid to the blood. The device 100 also includes (i) an inlet 401 for receiving a concentrate for adjusting the concentration of one or more component of the bulk replacement fluid, and (ii) a concentrate flow control element 415 in communication with the inlet 401 and configured to control the rate at which the concentrate is added to the replacement fluid or blood before the blood is returned to the patient. Preferably, the concentrate is added to the replacement fluid prior to the replacement fluid being added to the blood (as depicted) so that the concentrate may be mixed or diluted prior to being added to the blood. The device may include a mixer (not shown) to mix the concentrate and bulk replacement fluid prior to adding to the blood.

In the device depicted in FIG. 10, the control electronics 150 are operably coupled to the concentrate flow control element 415 and are configured to control the rate at which the concentrate flow control element 415 adds fluid to the replacement fluid or blood based on data received from one or more sensors 200 that monitor a cardiovascular condition (e.g., as described above). By controlling the rate at which the concentrate is introduced into replacement fluid or blood, the concentration of a component, such as an electrolyte, of the returned blood can be controlled.

Referring now to FIG. 11, in which components that are numbered the same as in FIG. 10 refer to the same or similar components, a schematic block diagram of selected components of a blood fluid removal device 100 is shown. In the embodiment depicted in FIG. 11, the device has in inlet 110 for receiving blood from a patient, a blood flow control element 120 in communication with the inlet 110 and configured to control the rate at which blood flows through medium 130 for removing fluid and contaminates from the blood. The device also includes an outlet 140 in communication with the medium 130 for returning blood to the patient. In the depicted embodiment, the medium 130 includes a semipermeable filter 135, such as a hemodialysis or hemodiafiltration filter. The membrane separates a blood flow compartment from a dialysis flow compartment of the medium component 130.

In the embodiment depicted in FIG. 11, used dialysate is regenerated by passing through dialysate regeneration medium 402 or components, such REDY regeneration medium and components, or the like, to regenerate bulk dialysate. The device also has an outlet 180 in communication with the medium 130 for diverting fluid removed from the blood out of the device. A flow regulator element 700, such as a valve, is operably coupled to control electronics 150 and is disposed in the flow path between the medium 130 and the outlet 180 to control the amount of fluid that exits the device (as a portion of the fluid is regenerated). A concentrate containing a concentrated component, such as one or more electrolytes, may be added to the regenerated dialysate before the dialysate re-enters the medium 130.

In the depicted embodiment, the concentrate 410 is stored in a reservoir 410, having an inlet 401 that allows the concentrate supply in the reservoir 410 to be replenished from time to time. The rate at which the concentrate is added to the regenerated dialysate is controlled by concentrate flow control element 415, which is operably coupled to control electronics 150, and is based on data received from sensor 200 that monitors pH or electrolyte concentrations (e.g., as described above).

The device 100 in FIG. 11 also has a dialysis flow control element 170 for controlling the rate at which dialysis is introduced into the dialysis flow compartment of the medium 130.

In the depicted embodiment, the device 100 also includes a negative pressure control element 190 in communication with the dialysate compartment of the medium component 130. The negative pressure control element 190, which may include a pump or the like, may be used to generate or change a pressure differential across the membrane to control the rate at which fluid is removed from blood that passes though the medium component 130.

The control electronics 150, which may include a processor, memory, etc., are operably coupled to, and configured to control, the blood flow control element 120, the dialysis flow control element 170, and the negative pressure control element 190. By controlling these elements in a coordinated manner, the rate at which fluid is removed from blood may be controlled. It will be understood that a device 100 need not have all of the controllable elements (120, 170, 190) depicted in FIG. 11 to effectively control rate of fluid removal from blood.

Any suitable control element may be used for the various control elements (120, 150, 170, 195, 415) depicted in FIGS. 10-11. For example, a variable or adjustable rate pump may be employed. Alternatively or in addition, a series of electronically controllable valves may be employed. In some embodiments, the valves are in communication flow paths having differing flow resistances.

It will be understood that the blood fluid removal devices and systems, and components thereof, described herein are presented for purposes of illustration and not limitation. Components, devices and systems other than those described herein, or derivations of the components, devices and systems described herein, may be employed. Further, it will be understood that, while many of the blood fluid removal devices depicted in a variety of the figures, such as FIGS. 1-3, are shown as external to the patient, the teachings presented herein apply if the device, or components thereof, were implanted in the patient.

The devices and systems described above, or components thereof, may be used to carry out the methods depicted in FIGS. 12-13 and described below, or portions thereof. Of course, any suitable device or system may be employed to carry out the methods, or portions thereof, described below. It will be understood that various steps of the methods presented with regard to any one of FIGS. 12-13 below may be interchanged, substituted, or added to steps presented with regard to any other of FIGS. 12-13.

Figure 12:
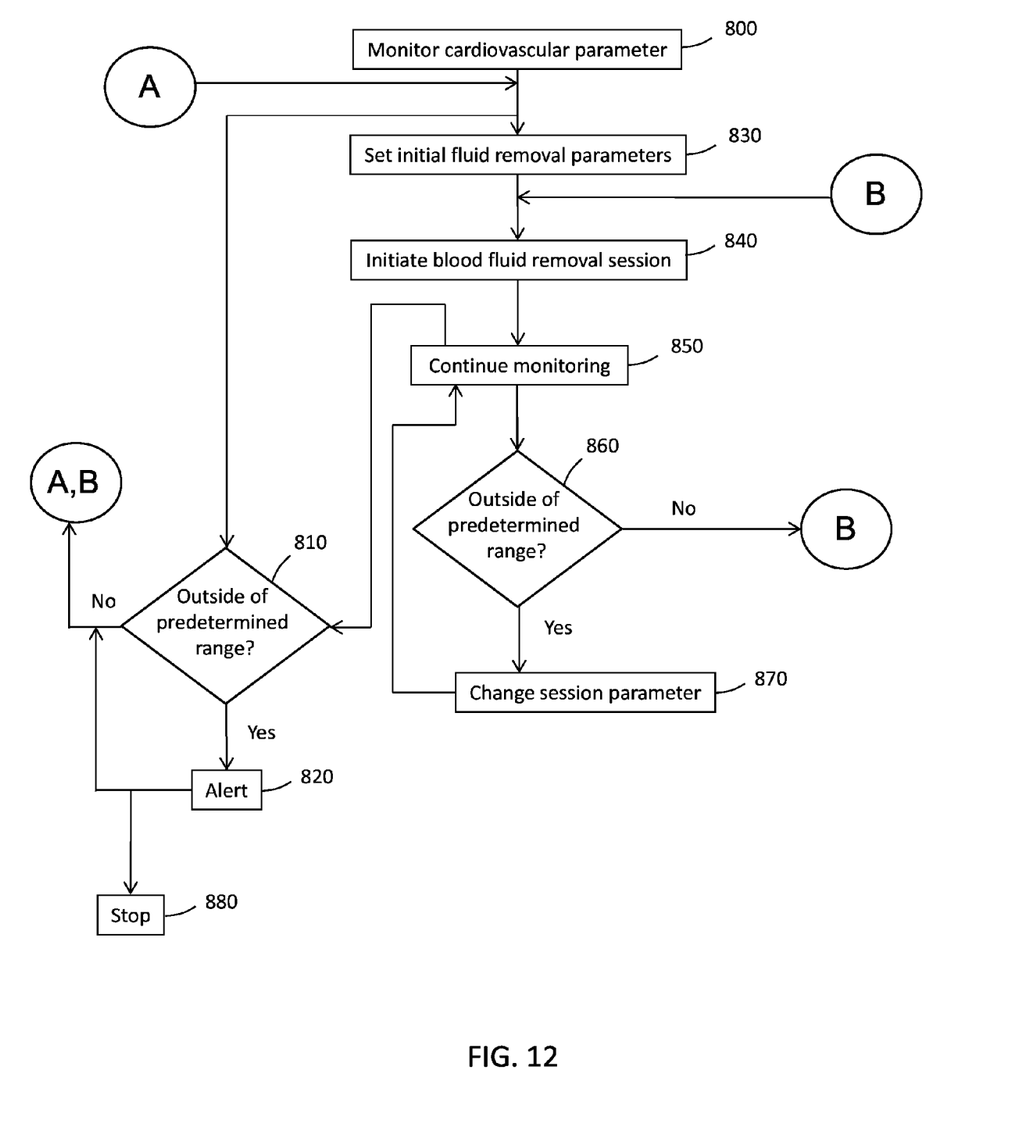
FIGS. 12-13 are flow diagrams illustrating overviews of general methods in accordance with embodiments described herein.

Referring now to FIG. 12, the depicted method includes monitoring a cardiovascular parameter of the patient (800); e.g. as discussed above. The monitoring (800) may be chronic and may employ one or more implantable or wearable sensors. The method further includes determining whether the monitored cardiovascular parameter is outside of a predetermined range (810). If the parameter is determined to be outside of the predetermined range, an alert may be issued (820). The alert may be an alert to the patients, such as a vibration or audible alarm emitted from the sensor or a device in communication with the sensor. The alert may be an alter to a healthcare provider, which may be transmitted from sensor or device in communication with sensor to a device in communication with the healthcare provider over the internet, a suitable phone network, or the like. A fluid removal session may be automatically scheduled.

If the monitored cardiovascular parameter is determined to not be outside the range (or in some cases, even if it is outside the range), data acquired during monitoring (800) is used to set initial parameters of a blood fluid removal session are set (830). The initial parameters of the session may include blood fluid removal rate, profile, or amount, the composition and concentration of components of fluid used during the session, such as dialysate or replacement fluid, and the like. As described above, the ability to chronically cardiac parameters of the patient provides the ability to tailor the parameters of a blood fluid session prior to each session, as opposed to current standard practice in which the fluid composition is adjusted on a monthly basis (or thereabout). As multiple blood fluid removal sessions (e.g., two to three a week) may occur with a month, setting the session parameters on a monthly basis may result in the patient undergoing several blood fluid removal sessions with session parameters that may no longer be well suited for the patient.

Still referring to FIG. 12, once the initial session parameters are set (830), the blood fluid removal session may be initiated (840) and monitoring of the cardiovascular parameters continued (850). A determination may be made as to whether the monitored cardiovascular parameter is outside of a first, higher threshold range (810) or a second, lower threshold range (860). If the parameter is outside of the first range (810), an alert (820) may be provided (e.g., as discussed above) and, in some cases, the blood fluid removal session may be stopped (880). If the cardiovascular parameter is not outside of the first range (810) but is outside the second range (860), a parameter of the blood fluid session may be changed (870) based on the monitored cardiovascular parameter (e.g., as discussed above). Further changes may be made in a similar manner as needed.

If the cardiovascular parameter is not outside of the first range (810) or the second range (860), the blood fluid session may continue with the initially set parameters.

Figure 13:
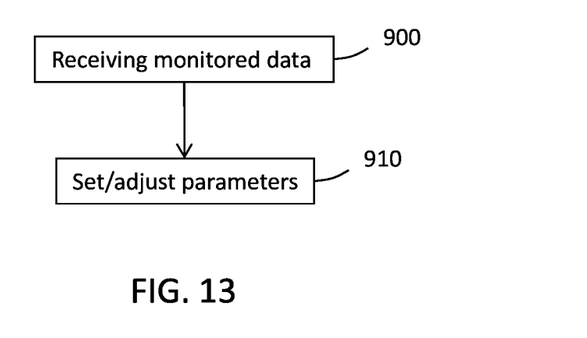

Referring now to FIG. 13, a method carried out by a blood fluid removal system or device is shown. The method includes receiving data regarding a monitored cardiovascular parameter (900) and setting or adjusting a parameter of a blood fluid removal session based on the received data. The system or device has control electronics configured to set or adjust the session parameter based on the received data regarding the cardiovascular parameter.

Many of the methods described herein, including the methods depicted in FIG. 12, or portions thereof, may be carried out by sensor devices, blood fluid removal devices, or other devices in communication with sensor devices or blood fluid removal devices. These methods may be algorithms or instructions programmed into memory of such devices, which may be carried out by processors or other control electronics of the devices. Preferably, the processor is in communication with appropriate control elements of the devices and is configured to control such elements in a manner such that the programmed instructions are carried out by the appropriate device. It will be understood that a computer readable medium programmed with instructions that cause a sensor device, blood fluid removal device, or other suitable device to carry out a method, or a portion thereof, as described herein are contemplated. The computer readable medium may be non-transitory, i.e. lasting for more than a fleeting instant or seconds. The medium may be memory, such as RAM or ROM, a cd or dvd, flash memory, or the like.

A variety of aspects of methods, devices, systems, computer-readable media, etc. are described herein. A summary of some aspects is provided below.

In a first aspect a method carried out by a blood fluid removal device or system comprises (i) initiating a blood fluid removal session for a patient in need thereof; (ii) monitoring a cardiovascular parameter of the patient; (iii) determining whether the indicator of the cardiovascular state crosses a predetermined threshold; and (iv) altering a parameter of the blood fluid removal session if the indicator is determined have crossed the threshold.

A second aspect is a method of aspect 1, wherein the predetermined threshold is based on measurements of the cardiovascular parameter obtained prior to initiating the blood fluid removal session.

A third aspect is a method of aspect 1 or 2, further comprising monitoring the cardiovascular parameter of the patient prior to initiating the blood fluid removal session, and setting an initial prescription for the blood fluid removal session based on the cardiovascular parameter monitored prior to initiating the blood fluid removal session.

A fourth aspect is a method of aspect 3, wherein the setting the initial prescription for the blood fluid removal session comprises setting a fluid removal prescription or setting a dialysate composition prescription.

A fifth aspect is a method of aspect 4, wherein monitoring the cardiovascular parameter of the patient prior to initiating the blood fluid removal session comprises chronically monitoring the cardiovascular parameter.

A sixth aspect is a method of aspect 5, further comprising (i) determining whether the cardiovascular parameter crosses a predetermined threshold, and (ii) scheduling the blood fluid removal session or providing an alert if the parameter crosses the threshold.

A seventh aspect is a method of any of aspects 1-6, wherein monitoring the cardiovascular parameter comprises monitoring one or more of heart rate, heart rhythm or blood pressure.

An eighth aspect is a method of any of aspects 1-7, wherein altering the parameter of the blood fluid removal session comprises altering the rate of removal of fluid from the patient's blood.

A ninth aspect is a method of any of aspects 1-8, wherein altering the parameter of the blood fluid removal session comprises altering a concentration of a component of a fluid selected from dialysate or replacement fluid.

A tenth aspect is a method carried out by a blood fluid removal device or system, comprising: (i) receiving data regarding a monitored cardiovascular parameter to a blood fluid removal device or system; and (ii) setting a parameter for a blood fluid removal session based on the received data regarding the monitored cardiovascular parameter, wherein the parameter is set by control electronics of a blood fluid removal device or system.

An eleventh aspect is a method of aspect 10, wherein setting the initial prescription for the blood fluid removal session comprises setting a fluid volume removal prescription.

A twelfth aspect is a method of aspect 10 or 11, wherein setting the initial prescription for the blood fluid removal session comprises setting a dialysate composition or a replacement fluid composition.

A thirteenth aspect is a method of any of aspects 10-12, wherein the cardiovascular parameter comprises one or more of heart rate, heart rhythm and blood pressure.

A fourteenth aspect is a system comprising: (a) a blood fluid removal device comprising (i) an inlet for receiving blood from a patient, (ii) an outlet for returning blood from the patient, (iii) a medium for removing fluid and contaminants from the blood, the medium being positioned between the inlet and the first outlet, and (iv) a control element for controlling the rate at which fluid is removed from the blood by the medium; (b) a sensor for monitoring a cardiovascular parameter of the patient; and (c) control electronics in operable communication with the sensor and the control element, wherein the control electronics are configured, via the control element, to adjust the rate at which the fluid is removed from the blood.

A fifteenth aspect is a system of aspect 14, wherein the blood fluid removal device further comprises a fluid source for carrying a system fluid, the system fluid selected from dialysate and replacement fluid, wherein if the fluid is dialysate the fluid source carries the fluid to the medium, and wherein if the fluid is replacement fluid the fluid source carries the fluid to the blood after the blood exits the medium; wherein the system further comprises (i) a concentrate source for housing a concentrate solution comprising a concentrated component for the system fluid; and (ii) a concentrate flow control element for controlling the rate that the concentrate solution enters the fluid source, wherein the sensor is operably coupled to the control electronics and the control electronics are further configured, via the concentrate flow control element, to adjust the rate at which the concentrate solution enters the fluid source based on data obtained from the sensor.

A sixteenth aspect is a system of aspect 14 or 15, wherein the control electronics are housed within the blood fluid removal device.

A seventeenth aspect is a system comprising: (a) a blood fluid removal device comprising (i) an inlet for receiving blood from a patient, (ii) an outlet for returning blood from the patient, (iii) a medium for removing fluid and contaminants from the blood, the medium being positioned between the inlet and the first outlet, and (iv) a fluid source for carrying a fluid, the fluid selected from dialysate and replacement fluid, wherein if the fluid is dialysate the fluid source carries the fluid to the medium, and wherein if the fluid is replacement fluid the fluid source carries the fluid to the blood after the blood exits the medium; (b) a concentrate source for housing a concentrate solution comprising a concentrated component for the fluid; (c) a concentrate flow control element for controlling the rate that the concentrate solution enters the fluid source; (d) a first sensor for monitoring a cardiovascular parameter of the patient; and (e) control electronics in operable communication with the sensor and the concentrate flow control element, wherein the control electronics are configured, via the concentrate flow control element, to adjust the rate at which the concentrate solution enters the fluid source based on data obtained from the sensor.

An eighteenth aspect is a system of aspect 17, wherein the control electronics are housed within the blood fluid removal device.

A nineteenth aspect is a system of any of aspects 14-18, further comprising a computer readable medium, wherein the computer readable medium comprises instructions that cause the control electronics to control the concentrate flow control element to adjust the rate at which the concentrate solution enters the fluid source based on data obtained from the sensor.

A twentieth aspect is a method carried out by a blood fluid removal device or system, comprising: (i) receiving data regarding a monitored cardiovascular parameter to a blood fluid removal device or system; and (ii) aborting a blood fluid removal session based on the received data regarding the monitored cardiovascular parameter.

A twenty-first aspect is a method of aspect 20, wherein the blood fluid removal session is aborted before the beginning of the session.

Thus, systems, devices and methods for CARDIOVASCULAR MONITORING FOR FLUID REMOVAL PROCESSES are described. Those skilled in the art will recognize that the preferred embodiments described herein may be altered or amended without departing from the true spirit and scope of the disclosure, as defined in the accompanying claims.

What is claimed is:

1. A method carried out by a blood fluid removal device or system, comprising:
    initiating a blood fluid removal session for a patient in need thereof;
    monitoring a cardiovascular parameter and at least one additional physiological parameter of the patient with at least one sensor;
    determining whether an indicator of the cardiovascular parameter or physiological parameter crosses a predetermined threshold; and
    altering a parameter of the blood fluid removal session if the indicator is determined to have crossed the threshold, wherein the blood fluid removal device comprises control electronics, wherein the control electronics are configured to control one or more flow control elements to adjust a pH or electrolyte concentration of a replacement fluid based on the data from the at least one sensor; and
    wherein altering a parameter of the blood fluid removal session comprises setting or adjusting the pH and electrolyte concentration of the replacement fluid based at least on the cardiovascular or physiological parameter of the patient wherein the step of altering the parameter of the blood fluid removal session is carried out by the blood fluid removal device.

2. The method of claim 1, wherein the predetermined threshold is based on measurements of the cardiovascular parameter obtained prior to initiating the blood fluid removal session.

3. The method of claim 1, further comprising monitoring the cardiovascular parameter of the patient prior to initiating the blood fluid removal session, and setting an initial prescription for the blood fluid removal session based on the cardiovascular parameter monitored prior to initiating the blood fluid removal session.

4. The method of claim 3, wherein setting the initial prescription for the blood fluid removal session comprises setting a fluid removal prescription or setting a dialysate composition prescription.

5. The method of claim 4, wherein monitoring the cardiovascular parameter of the patient prior to initiating the blood fluid removal session comprises chronically monitoring the cardiovascular parameter.

6. The method of claim 5, further comprising (i) determining whether the cardiovascular parameter crosses a predetermined threshold, and (ii) scheduling the blood fluid removal session or providing an alert if the parameter crosses the threshold.

7. The method of claim 1, wherein monitoring the cardiovascular parameter comprises monitoring one or more of heart rate, heart rhythm or blood pressure.

8. The method of claim 1, wherein altering the parameter of the blood fluid removal session comprises altering the rate of removal of fluid from the patient's blood.

9. The method of claim 1, wherein altering the parameter of the blood fluid removal session comprises altering a concentration of a component of a fluid selected from dialysate or replacement fluid.

10. A method carried out by a blood fluid removal device or system, comprising:

receiving data regarding a monitored cardiovascular parameter and at least one additional physiological parameter to a blood fluid removal device or system; wherein the blood fluid removal device comprises control electronics, wherein the control electronics are configured to control one or more flow control elements to adjust a pH or electrolyte concentration of a replacement fluid based on the data from the at least one sensor; and setting a parameter for a blood fluid removal session based on the received data regarding the monitored cardiovascular or physiological parameter, wherein the parameter for the blood fluid removal session is set by control electronics of a blood fluid removal device or system, wherein setting the parameter for the blood fluid removal session comprises setting or adjusting the pH and electrolyte concentration of a replacement fluid based at least on the monitored physiological parameter, and wherein setting the parameter for the blood fluid removal session is carried out by the blood fluid removal device.

11. The method of claim 10, wherein the cardiovascular and at least one physiological parameter of the patient are used in setting an initial prescription for the blood fluid removal session, wherein setting an initial prescription for the blood fluid removal session comprises setting a fluid volume removal prescription.

12. The method of claim 10, wherein setting an initial prescription for the blood fluid removal session comprises setting a dialysate composition or a replacement fluid composition.

13. The method of claim 10, wherein the cardiovascular parameter comprises one or more of heart rate, heart rhythm and blood pressure.

14. A system comprising:
a blood fluid removal device comprising
(i) an inlet for receiving blood from a patient,
(ii) an outlet for returning blood to the patient,
(iii) a medium for removing fluid and contaminants from the blood, the medium being positioned between the inlet and the outlet, and
(iv) a control element for controlling the rate at which fluid is removed from the blood by the medium;
a sensor for monitoring a cardiovascular parameter and at least one additional physiological parameter of the patient; and
control electronics in operable communication with the sensor and the control element, wherein the control electronics are configured, via the control element, to adjust the rate at which the fluid is removed from the blood, and wherein the pH and electrolyte concentration of a replacement fluid can be set or adjusted based at least on a cardiovascular or physiological parameter of the patient by the blood fluid removal device.

15. The system of claim 14, wherein the blood fluid removal device further comprises a fluid source for carrying a system fluid, the system fluid selected from dialysate and replacement fluid, wherein if the fluid is dialysate the fluid source carries the fluid to the medium, and wherein if the fluid is replacement fluid the fluid source carries the fluid to the blood after the blood exits the medium; wherein the system further comprises
a concentrate source for housing a concentrate solution comprising a concentrated component for the system fluid; and
a concentrate flow control element for controlling the rate at which the concentrate solution enters the fluid source;
wherein the sensor is operably coupled to the control electronics and the control electronics are further configured, via the concentrate flow control element, to adjust the rate at which the concentrate solution enters the fluid source based on data obtained from the sensor.

16. The system of claim 14, wherein the control electronics are housed within the blood fluid removal device.

17. A system comprising:
a blood fluid removal device comprising
(i) an inlet for receiving blood from a patient,
(ii) an outlet for returning blood to the patient,
(iii) a medium for removing fluid and contaminants from the blood, the medium being positioned between the inlet and the outlet, and
(iv) a fluid source for carrying a fluid, the fluid selected from dialysate and replacement fluid, wherein if the fluid is dialysate the fluid source carries the fluid to the medium, and wherein if the fluid is replacement fluid the fluid source carries the fluid to the blood after the blood exits the medium;
a concentrate source for housing a concentrate solution comprising a concentrated component for the fluid;
a concentrate flow control element for controlling the rate at which the concentrate solution enters the fluid source;
a sensor for monitoring a cardiovascular parameter and at least one additional physiological parameter of the patient; and
control electronics in operable communication with the sensor and the concentrate flow control element,
wherein the control electronics are configured, via the concentrate flow control element, to adjust the rate at which the concentrate solution enters the fluid source based on data obtained from the sensor, and wherein the pH and electrolyte concentration of a replacement fluid can be set or adjusted based at least on the physiological parameter of the patient by the blood fluid removal device.

18. The system of claim 17, wherein control electronics are housed within the blood fluid removal device.

19. The system of claim 16, further comprising a non-transitory computer readable medium, wherein the computer readable medium comprises instructions that cause the control electronics to control the concentrate flow control element to adjust the rate at which the concentrate solution enters the fluid source based on data obtained from the sensor.

* * * * *